United States Patent [19]
Janese

[11] Patent Number: 5,183,058
[45] Date of Patent: Feb. 2, 1993

[54] CEPHALIC EXPANSION APPARATUS AND THE METHOD OF USING TO TREAT HEAD INJURY

[76] Inventor: Woodrow W. Janese, Janus Medical Instruments, 2806 N. Navaro, Suite M, Room B, Victoria, Tex. 77901

[21] Appl. No.: 747,723

[22] Filed: Aug. 19, 1991

Related U.S. Application Data

[63] Continuation-in-part of Ser. No. 560,014, Jul. 27, 1990, abandoned, which is a continuation of Ser. No. 205,250, Jun. 10, 1988, abandoned.

[51] Int. Cl.$^5$ .............................................. A61F 13/00
[52] U.S. Cl. .................................... 128/847; 128/857; 128/898; 604/355; 600/21
[58] Field of Search ....................... 604/19, 21, 22, 49, 604/27, 289, 290, 303, 355, 356; 600/21, 37; 128/97.1, 163, 303 B, 379, 380, 402, 845–847, 849, 850, 852, 853, 857, 887, 897, 898

[56] References Cited

U.S. PATENT DOCUMENTS

| | | | |
|---|---|---|---|
| 2,320,467 | 6/1943 | Rabi | 128/402 |
| 2,507,386 | 5/1950 | Spiegel | 604/289 |
| 2,858,834 | 11/1958 | Givens | 128/380 |
| 3,060,932 | 10/1962 | Pereny et al. | 128/849 |
| 3,288,140 | 11/1966 | McCarthy | 604/289 |
| 4,367,728 | 1/1983 | Mutke | 128/853 |

FOREIGN PATENT DOCUMENTS

| | | | |
|---|---|---|---|
| 0114443 | 12/1941 | Australia | 128/248 |
| 1566382 | 4/1970 | Fed. Rep. of Germany | 128/335 |
| 0641061 | 8/1950 | United Kingdom | 604/289 |

OTHER PUBLICATIONS

Guyton, *Anatomy and Physiology*, pp. 243–244.
Guyton, *Human Physiology and Mechanisms of Disease*, 4th ed. 1987 p. 259.
Dunphy, and Way, Current Surgical Diagnosis and Treatment, 1981, pp. 709–710.
Surg. Gyn Obstet., Cushing, H., 1:297–315 (1905).
Ann Surg., Hudson, W. H., 55:744–749 (1912).
J. Neurosurg, Clark, K., Nash, T. M. and Hutchison, G. C., 29:367–371 (1968).
Mayo Clin Proc, Kerr, F. W. L., 43:852–864 (1968).
J. Neurosurg, Ransohoff, J., Benjamin, M. W., Gage, E. L. and Epstein, F., 34:70–76 (1971).
J. Neurosurg, Kjellberg, R. N. and Prieto, A., 34:488–493 (1971).
J. Neurosurg, Venes, J. L. and Collins, W. F., 42:429–33 (1975).
Acta Neurochirurgica, Ito, U., Tomita, H., Yamazaki, Sh., Takada Y. and Inaba, Y., 79:120–124 (1986).
British Medical Journal, Richards, P., 293:643 (1986).
Am Surg, Walker, E. A. and Black, P., 26:184–188 (1960).
Deutsch Z. Chir, Bauer, K. H., 237:402–421, (1932).
JAMA, Spiller, U. G. and Frazier, C. H., 47:679–683, 744–751, 849–853, 923–926 (1906).
J. Neurosurgery, Bruce, D. A., 54:170–178 (1981).
Journal of Neurosurgery, Becker, D. P. and Miller, J. D., 47:491–502 (1977).
Journal of Neurosurgery, Sahuquillo-Barnes, J., et al., 68:894–900 (1988).

*Primary Examiner*—John D. Yasko
*Assistant Examiner*—Anthony Gutowski
*Attorney, Agent, or Firm*—Vaden, Eickenroht, Thompson, Boulware & Feather

[57] ABSTRACT

An apparatus and method to treat head injury. The apparatus includes a cephalic expansion reservoir to allow a swollen brain to expand without increasing intracranial pressure. The apparatus has a port for fluid exchange and for the attachment of monitors of physical, chemical and electrical activity. The method includes attaching the apparatus to the skin with biological adhesives, removing the bone for replacement after treatment, treating the injured patent with appropriate therapy including filling the expansion reservoir with an appropriate fluid.

18 Claims, 7 Drawing Sheets

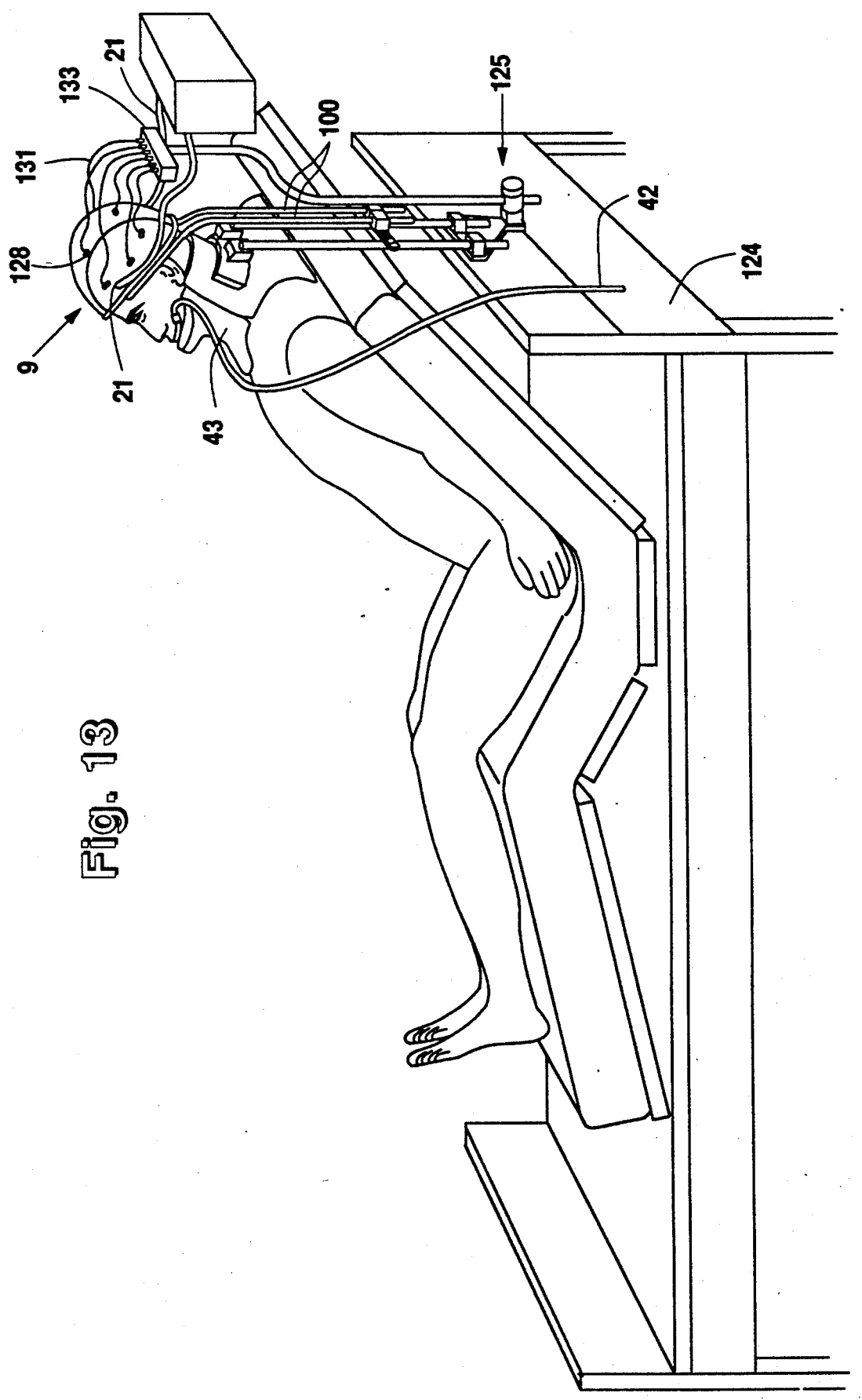

CEPHALIC EXPANSION APPARATUS AND THE METHOD OF USING TO TREAT HEAD INJURY

This application is a continuation in part of 07/560,014 filed Jul. 27, 1990 (abandoned), which is a continuation of 07/205,250 filed Jun. 10, 1988 (abandoned).

FIELD OF THE INVENTION

The present invention relates generally to an apparatus and a method for treating severe head injury. The apparatus is a flexible container which adapts to the skull contour of an injured patient. The flexible container allows the injured swollen brain to expand into a sterile chamber of fluid. Furthermore, there are ports for access to the flexible container for the exchange of fluid and the monitoring of the patient's status. The apparatus and the procedures can be used to treat a variety of brain diseases and brain injury which result in swelling of the brain.

BACKGROUND OF THE INVENTION

Throughout history head injury has been very common and has occurred in all levels of society. When a force vector is directed through the head each layer of contact, that is, the skin, bone, and brain is affected proportionately to the force involved. The skin can be crushed, cut or abraded. The bone can be bruised, cracked or depressed. The brain can be concussed, bruised (contused) or lacerated. When the brain is contused or lacerated, swelling occurs. The swelling can result from injury or disruption to a variety of cellular components of the brain including the endothelial membranes of blood vessels, membranes or support cells of brain cells and cellular membranes of the neuron. The increase in intracranial pressure is proportional to the volume of brain injured. Standard methods of intensive care management, which include steriods, mannitol, head elevation, hyperventilation, and fluid restriction, are only partially successful in the treatment of serious head injuries. Even with these treatment regimes there is a mortality rate of greater than 50%.

It is known that the severity of head injury is directly proportional to the increased pressure inside the head cavity housing the brain. For example, if intracranial pressure greater than 20 Torr is present the mortality rate is estimated at 45%. Doubling the pressure to 40 Torr increases the mortality rate to 74%. Increasing the pressure to 60 Torr, results in a 100% mortality rate. These mortality figures assume that current neural intensive care has occurred. Thus, at present, there is no method of treatment which can successfully treat severe head injury except early diagnosis and decompression of epidural, subdural and intracerebral hematomata. Currently, only methods of prevention are helpful. Thus, although the use of seat belts, air bags, restricted ethanol intake, careful driving, etc. all result in fewer severe head injuries, none of these approaches are helpful after the injury has occurred.

Major head injury primarily affects young people between the ages of 15-40 years of age. They are in their most productive years and in many cases provide the major support for their families. Thus it is important that a successful method of treatment be developed. The cephalic expansion apparatus and method of the present invention provides a new treatment increasing the chances of survival after severe head injury with brain swelling.

SUMMARY OF THE INVENTION

An object of the present invention is the provision of an apparatus for allowing the brain to expand without injury.

An additional object of the present invention is the provision of an apparatus for monitoring the brain while allowing the brain to expand.

A further object of the present invention is the provision of an apparatus for the treatment of brain trauma.

Yet another object of the present invention is the provision of a method for the treatment of brain injury.

Thus, in accomplishing the foregoing objects one aspect of the present invention is an apparatus for the treatment of brain trauma comprising a flexible container for holding sterile fluid and allowing a swollen brain to expand. This flexible container can be attached to the scalp of the skull of an individual by the use of a biological adhesive. The biological adhesive forms a water-tight attachment between the container (polymer) and the skin (keratin). The apparatus contains a water-tight locking means for sealing the container after attachment to the head. Sterile fluid can be introduced into the sealed container through access ports. In addition, the access ports can receive cortical surface electrodes and other probes for monitoring the electrical, physical and chemical activity of the brain and surrounding fluid.

The invention also includes a method of treating severe head injury comprising the steps of preparing and sterilizing the scalp of the head. Applying adhesive strips to the scalp for forming a water-tight seal between the scalp, the adhesive strips and the flexible container which is attached to the scalp. Performing a craniotomy, removing the bone flaps and preserving the bone flaps for replacement after the treatment. Sealing the cephalic expansion apparatus by closing the flexible container. Filling the flexible container with a cooled, pH adjusted sterile fluid, and monitoring the physical, electrical and chemical parameters of the brain and the fluid during the treatment. Removing the cephalic expansion apparatus and replacing the bone flaps after the brain swelling has subsided.

Further objects features and advantages will be apparent from the following description of the preferred embodiment of the invention.

BRIEF DESCRIPTION OF THE DRAWINGS

So that the manner in which the above featured advantages and objects of the present invention will be more readily understood, a more particular description of the construction and operation may be had by reading the following specification and by references to the accompanying drawings forming a part thereof:

FIG. 13 is a schematic view of a patient in the neurological intensive care unit with a cephalic expansion apparatus and auxiliary neurological care structures attached.

DETAILED DESCRIPTION OF THE PREFERRED EMBODIMENTS

In the description which follows like parts are marked throughout the specifications and drawings with the same referenced numerals. The drawings are not necessarily to scale and certain features of the invention may be exaggerated in scale or shown in schematic form in the interest of clarity and conciseness. It will be readily apparent to one skilled in the art that various substitutes and modifications may be made to the invention disclosed herein, without departing from the scope and spirit of the invention.

Figure 1:
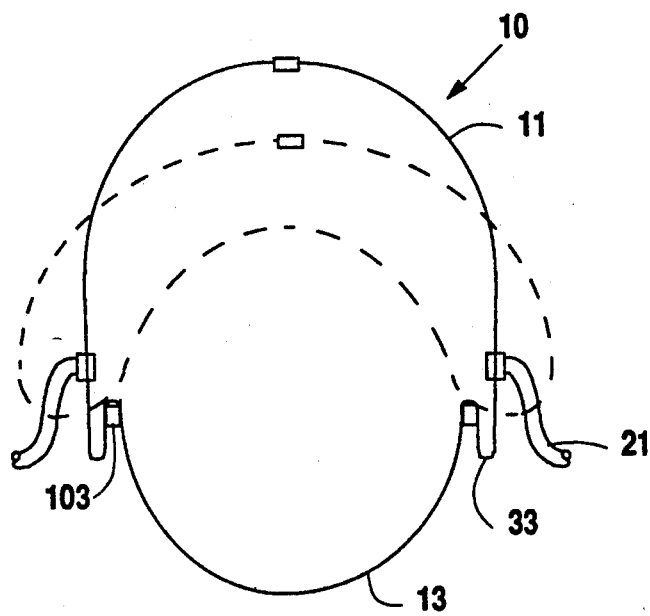
FIG. 1 is an anterior elevational view of a cephalic expansion apparatus.
Figure 2:
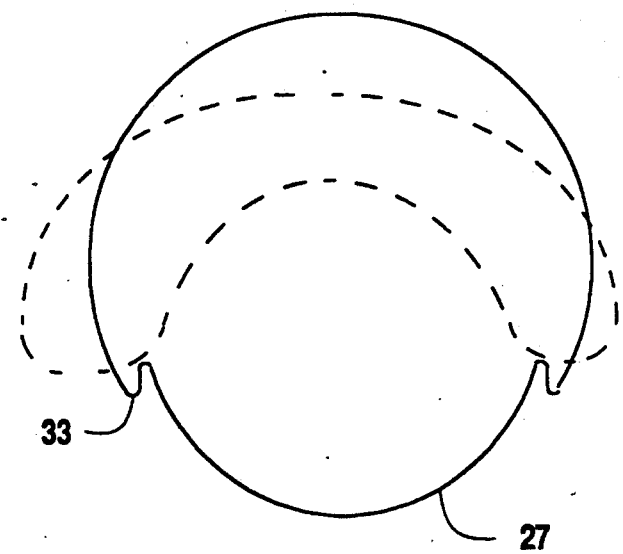
FIG. 2 is a lateral elevational view of a cephalic expansion apparatus.
Figure 3:
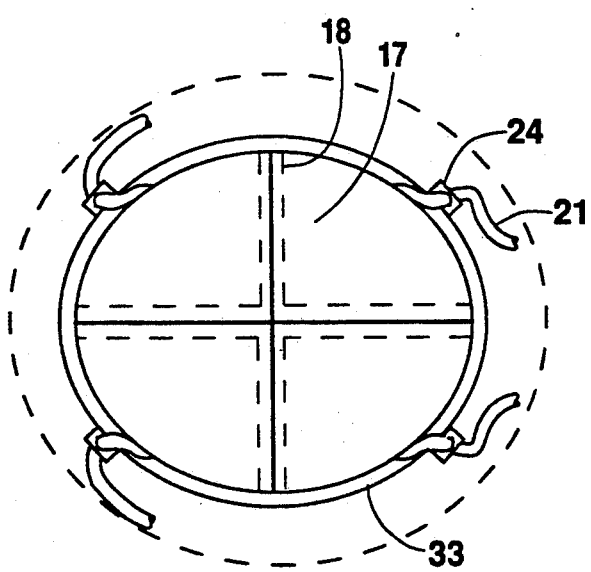
FIG. 3 is a superior elevational view of a cephalic expansion apparatus.
Figure 4:
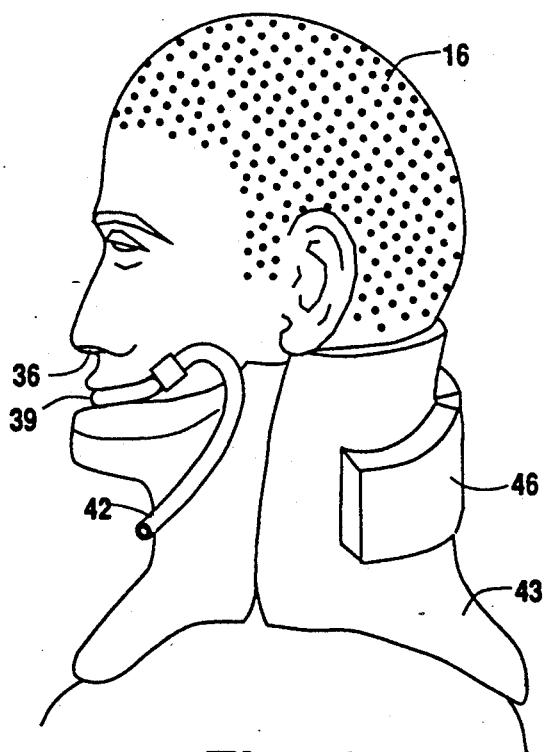
FIG. 4 is a schematic view of a prepared scalp.

FIGS. 1, 2, and 3 show the various parts of the cephalic expansion apparatus 9 including a flexible container 10 for holding sterile fluid and allowing a swollen brain to expand. The flexible container can be a variety of shapes and sizes to fit a head. In the preferred embodiment an elliptical shape is used. The upper side 11 of the unfilled flexible container is shown. The broken lines represent the shape of the flexible container when fluid filled and attached to a skull for treatment. The outer inferior surface 13 of the flexible container 10 is applied to a shaved, deoiled and adhesive prepared scalp 16 (FIG. 4). The inferior scalp contact section 17 of the flexible container 10 contains special scalp contact strips 18. These contact strips 18 include a special biological adhesive. Contact strips 18 are incised when the skin is incised. An irrigation tube 21 can be attached to a port 22 in the flexible container 10. The port 22 has reinforcement 24 to help support the irrigation tube. Although a single irrigation tube 21 and port 22 can be used the preferred embodiment includes a plurality of irrigation tubes 21 and ports 22. In the preferred embodiment the ports 22 and irrigation tubes 21 are located along the bottom of the flexible container 10. An expandable reinforceable flap 33 is located in a 360° direction directly adjacent to the scalp adhesive part 27 of the flexible container 10.

Figure 5:
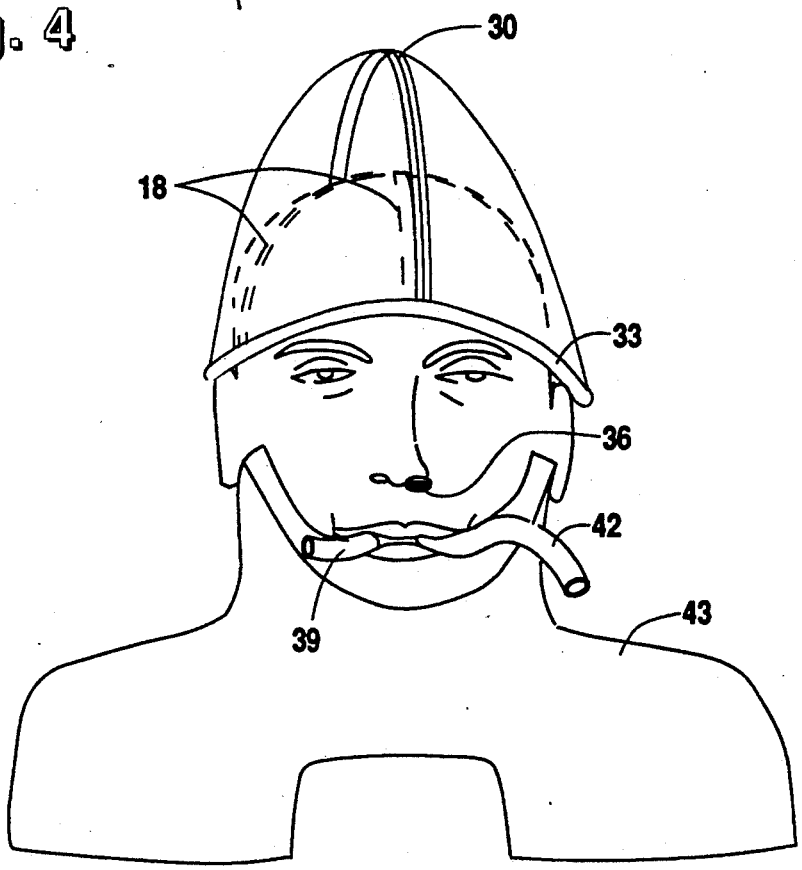
FIG. 5 is a perspective view of the initial application of the closed cephalic expansion apparatus to a prepared scalp.

When the flexible container 10 is applied, FIG. 5, to the scalp 16, the water-tight locking means 30 is initially closed. The adhesive strips 18 are applied in situ, and the inferior expansion flap 33 is folded down. A nasal canual 36, oral airway 39 and endotracheal tube 42 are also shown. A cephalo-cervical head rest 46 and collar support 43 are also shown.

Figure 7:
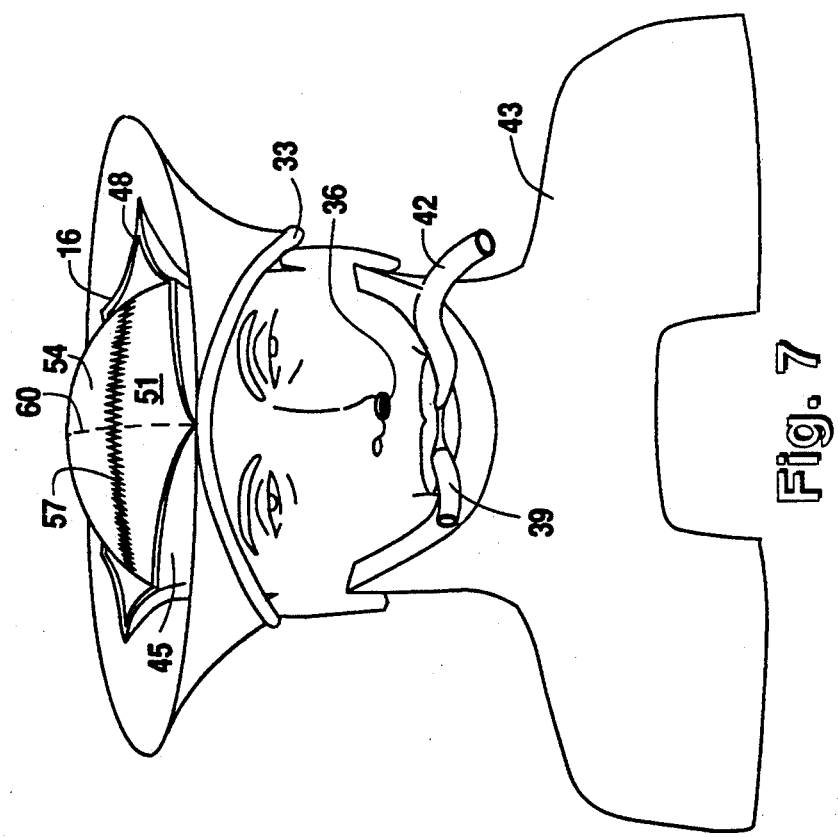
FIG. 7 is a perspective view of an exposed cranium with retracted scalp flaps.
Figure 6:
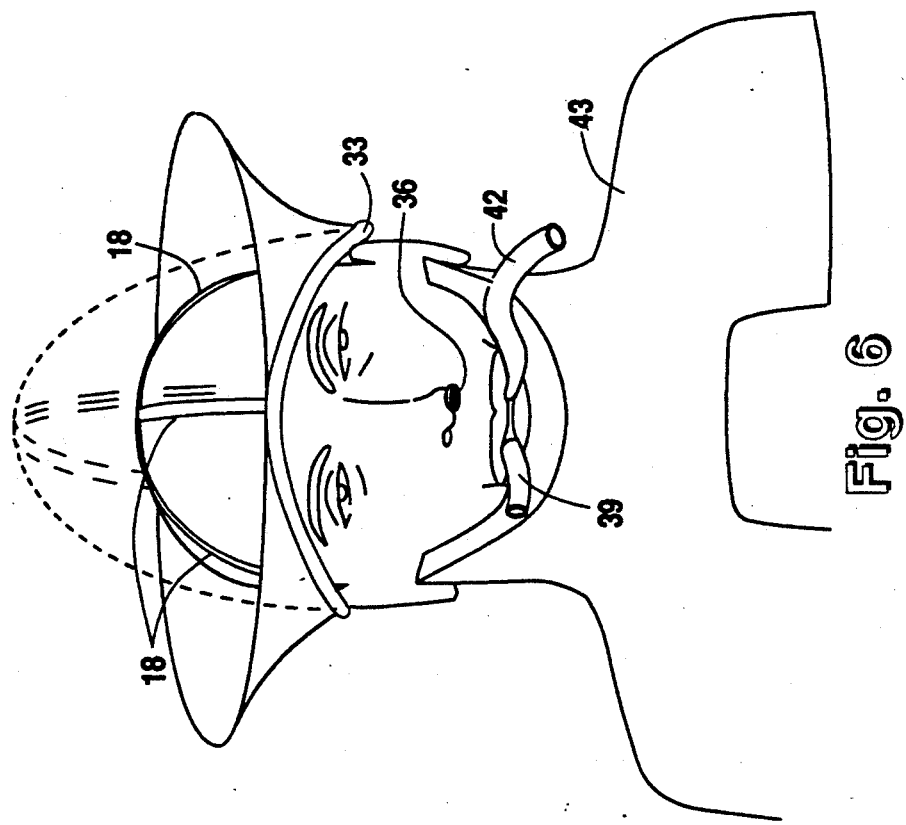
FIG. 6 is a perspective view of an opened cephalic expansion apparatus applied to the scalp.

In FIG. 6, the flexible container 10 is opened exposing the interior surface 45 of the inferior surface 13 which is adherent to the treated scalp 16. In FIG. 7 the special adhesive strip 18 and scalp 16 have been incised 48. The scalp 16 with the scalp contact section 17 of the flexible container 10 adhering by a water-tight bond have been retracted laterally. Hemostasis is accomplished by electrocautery. The frontal 51, parietal 54 and occipital calvaria are examined and the coronal 57 and sagittal sutures 60 are identified in preparation for craniotomy. The scalp is retracted 48 and sutured to the flexible container 10.

Figure 9:
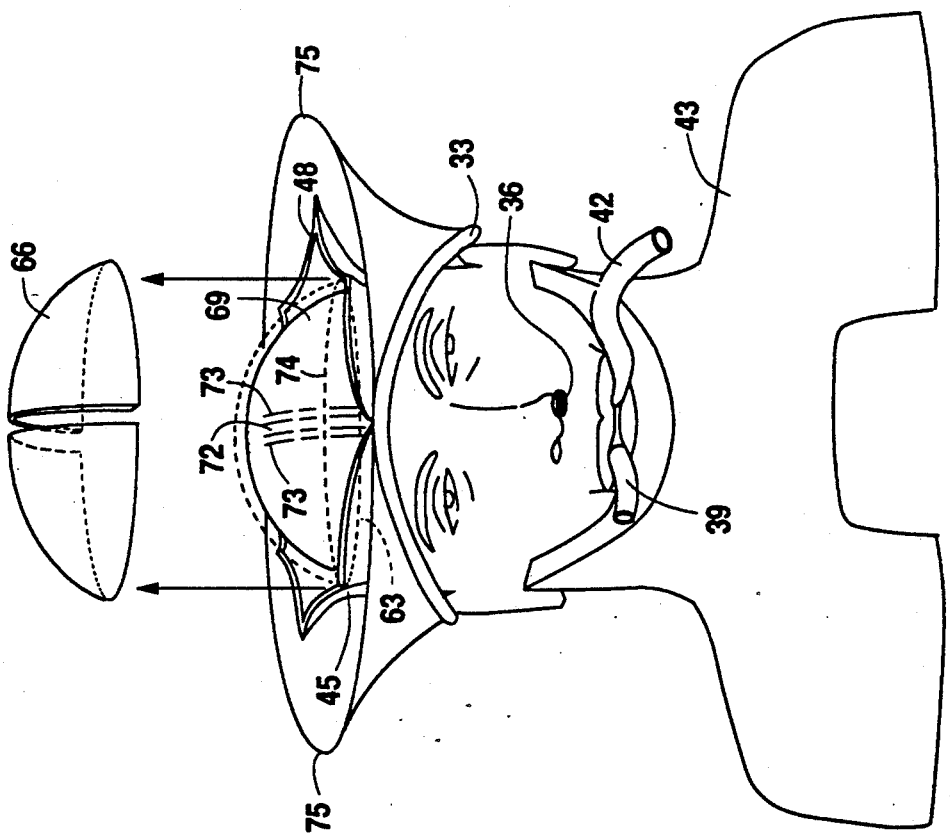
FIG. 9 is a perspective view of the removal of bone flaps after craniotomy.
Figure 8:
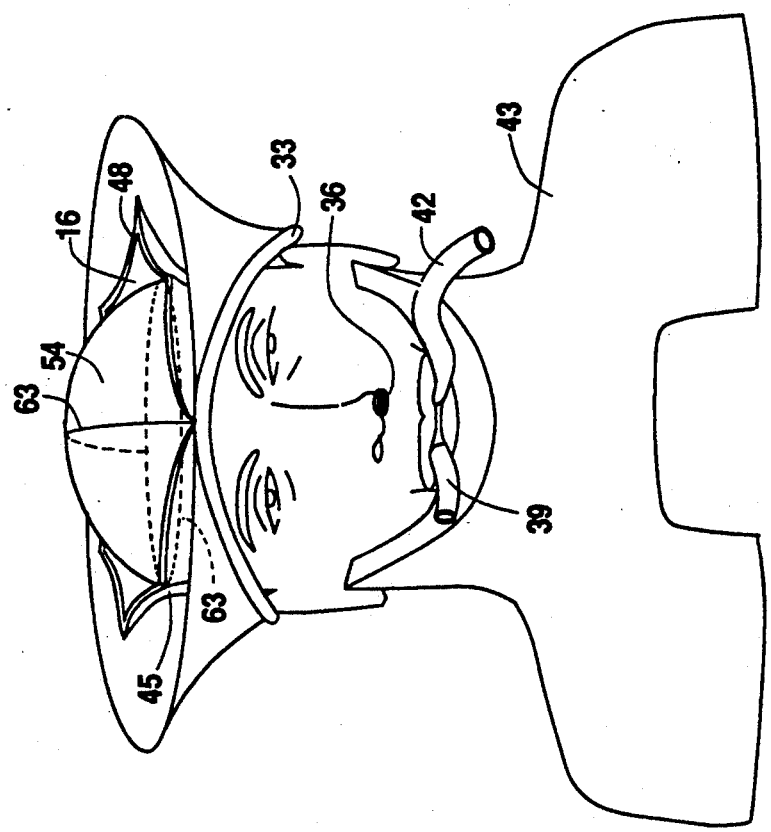
FIG. 8 is a perspective view of a craniotomy in situ.
Figure 10:
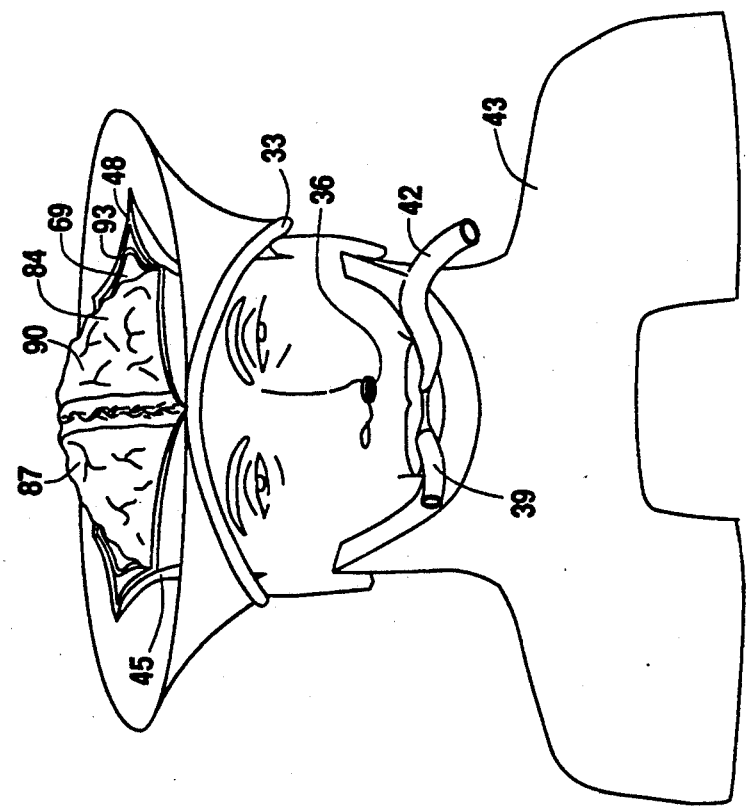
FIG. 10 is a perspective view of the exposed cerebral cortex.

FIG. 8 shows the line 63 along which the craniotomy is performed. In FIG. 9 the two free bone flaps 66 are carefully removed from the general dura 69 and dura over the superior sagittal sinus 72. Two bilateral parallel incisions 73 adjacent to the superior sagittal sinus 72 and two bilateral incisions 74 parallel to the coronal suture 57 are made and the dura 69 is opened and retracted laterally (FIG. 10). Hemostasis is accomplished by bipolar electrocautery. Generous amounts of 37° C. saline are used to irrigate the injured cortex 84. Swollen gyri 87 and sulci 90 are shown.

Figure 11:
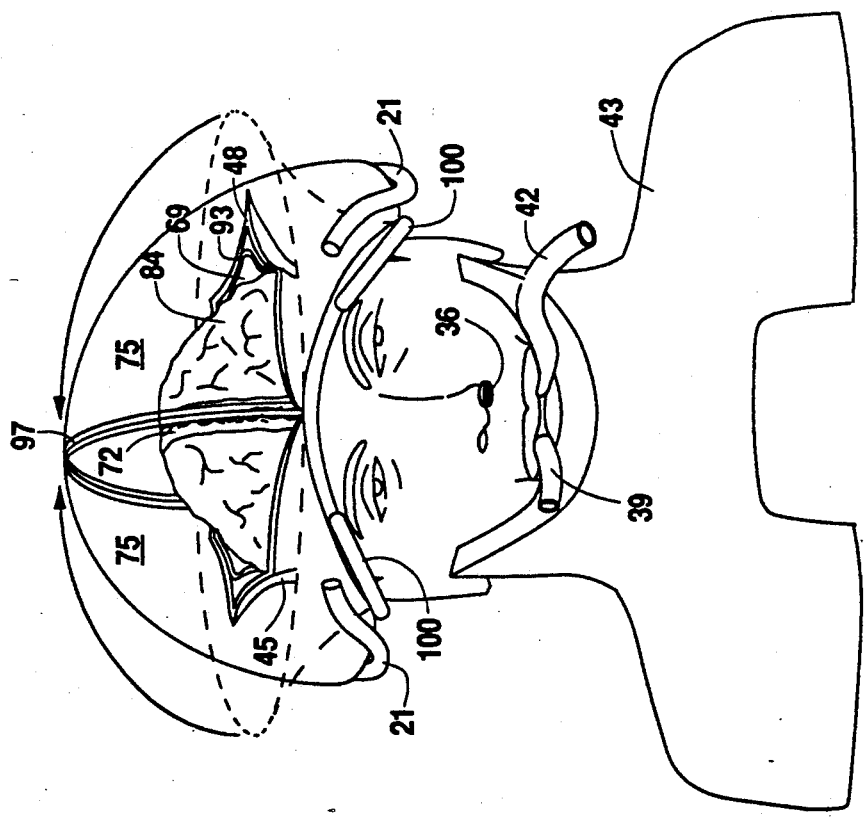
FIG. 11 is a perspective view of an engaged cephalic expansion apparatus prior to adding fluid.

After the dura 69 is sutured to the galea aponeurotica 93, the flexible container 10 is closed by bringing the two flaps 75 medially (e.g., in the direction of the arrows shown in FIG. 11). After observing for any bleeding the water-tight locking means 30, in the form of a groove locking device such as may be found on a conventional plastic bag of the type used for storing food and sold under the brand name "ZIP-LOC®", is engaged. Support ring 103 can be placed in the support rod 100 (see also FIGS. 13A and 13B) and secured to a stationary support.

An irrigation port 22 is used to exchange sterile fluid. In the preferred embodiment a plurality of ports 22 are incorporated into the flexible container 10. The irrigation ports 21 can be attached to devices which monitor and purify the fluid. In the preferred embodiment the fluid is saline, however, electrolytes and drugs can be added. The fluid can be processed by devices external to the cephalic expansion apparatus. For example the pH can be adjusted or the fluid can be cooled.

Figure 12:
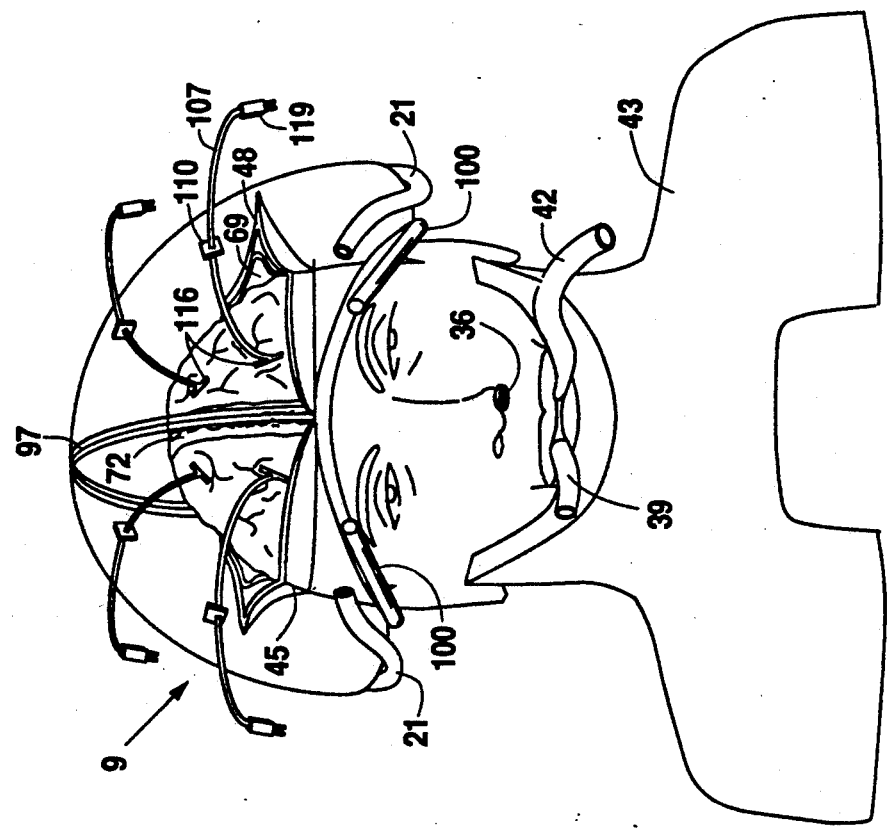
FIG. 12 is an elevational view of a cephalic expansion apparatus in situ with fluid and a plurality of attached cortical electrodes, support rods, and irrigation tubes.

Another enhancement to the cephalic expansion apparatus 9 is shown in FIG. 12. Here a plurality of cortical electrodes 107 are placed in reinforced rings 110. The leads 119 from the surface electrode grid 116 can be connected to a pre-amp and amplifier for surface EEG and evoked potential recordings.

In the preferred embodiment the cephalic expansion apparatus 9 holds approximately 7–9 liters of fluid. The fluid is preferably cooled, pH adjusted, filtered saline.

Figure 13B:
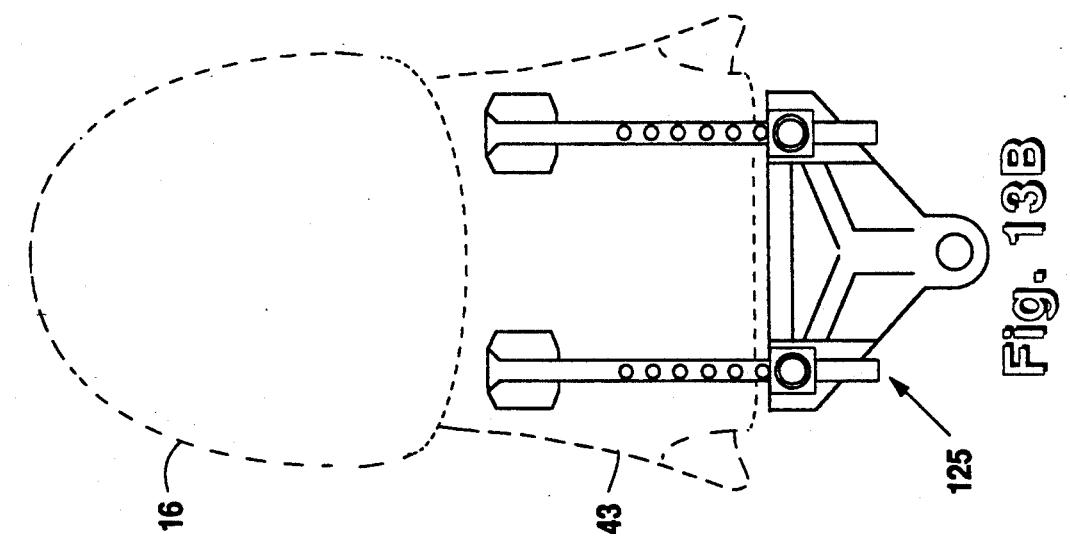
FIGS. 13A and 13B are plan views of the components of one embodiment of the apparatus for supporting the apparatus of FIG. 12, the component shown in FIG. 13A being shown disassembled from the components shown in FIG. 13B to show detail not apparent from FIG. 12.
Figure 13A:
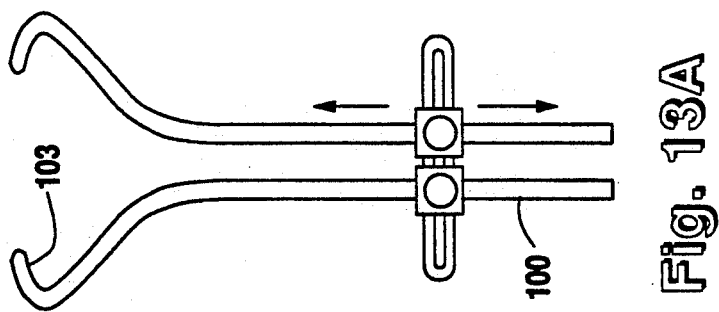

FIG. 13 shows a patient intubated in bed 124 with the cephalic expansion apparatus 9 attached. The patient's head is supported by a support means indicated generally in FIGS. 13 and 13B at reference numeral 125, and is elevated. In the treatment of severe head injury the head is elevated from about 30° to about 45°. In the preferred embodiment the head is elevated at about 45°. The cerebral expansion apparatus 9 is supported by support rod 100, which in turn supports the semi-circular rods 103. The surface electrodes 107 are made stationery by locking arms 128. The surface electrode grid wires 131 are secured by multi-pin sockets 133 and are channeled to a data acquisition area. One skilled in the art will recognize that a number of patient monitoring, and treatment devices can be attached to the patient and the cephalic expansion apparatus.

One embodiment of the cephalic expansion apparatus for the treatment of brain trauma comprises a flexible container for holding sterile fluid and allowing a swollen brain to expand. The flexible container can include a circumferential expansion flap for increasing the volume of flexible container. The external, inferior surface of the flexible container includes an adhesion means. The adhesion means, includes a biological adhesive for forming a water-tight bonding of the container to the skin. For example, alpha-cyanoacrylates can be used. A water-tight locking means is used for sealing the container. In the preferred embodiment the container is sterile when sealed. In the preferred embodiment a groove locking device is used. A support means for supporting the container and a port for access to the sealed container are also included.

Specific embodiments of the device in the preferred mode include a plurality of ports on the device for the irrigation of the chamber and for the insertion of monitor means for monitoring the brain. For example, cortical electrodes can be inserted into the device for monitoring brain surface electrical activity. The plurality of ports can have support rings attached to prevent inadvertent tube and probe movement and cortical injury. The ports are of a sufficient size to allow the attachment and insertion of tubes for the irrigation of the brain and to allow the attachment and insertion of monitor means. Furthermore, the ports can be connected to devices for monitoring, as well as, for exchanging the fluid in the brain. One skilled in the art will recognize that a variety of devices can be used to reduce the temperature, to adjust the pH, to filter the fluid and to add substances such as electrolytes and drugs for the treatment of infections or other medical, physical and chemical problems of the patient.

The cortical electrodes are moveable over the cortical surface and include surface attachments connected to a pre-amp. A locking means is used to prevent inadvertent electrode movement and cortical injury.

The cephalic expansion apparatus can be used to treat head injury. This method of treatment includes the attachment of the cephalic expansion apparatus to the scalp. In the preferred embodiment the shaved head of the patient receives a ten minute surgical scrub to minimize infection. The head is then aseptically prepared with an antiseptic solution and 90% alcohol. One skilled in the art will recognize that a variety of scrubbing and surgical preparation procedures are available. The preferred embodiment for scrubbing and sterilizing employees betadine and alcohol. The liquid alpha-cyanocrylate is spread on the alcohol prepared scalp in a thin layer. Strips of plastic polymer sheeting, for example polyethylene, are applied along the sagittal suture from the nasion to the inion and from midway between the coronal and lambdoidal sutures to the level of both tragi. After these strips adhere, the cephalic expansion apparatus is attached to the strips and scalp. The bonding of the cephalic expansion apparatus to the strips and scalp with a topical biological adhesive forms a water-tight seal between scalp and the cephalic expansion apparatus. The external, inferior surface of the cephalic expansion apparatus is applied with sufficient force to spread the liquid in a thin layer between the scalp and the flexible container. Usually about one drop of adhesive per square inch of skin is sufficient to cause adhesion in seconds. Sixty percent of the final bond strength occurs within 10 minutes. A standard craniotomy is then performed. The bone flaps are removed and preserved for replacement after the treatment of the brain injury. In the preferred embodiment the bone flaps are kept sterile and frozen at about 4.5° C. The cephalic expansion apparatus is sealed by closing the water-tight locking means. The closed cephalic expansion apparatus is then filled with pH adjusted fluid. The fluid is cooled with a temperature regulating means. The lower temperature facilitates recovery. In the preferred embodiment the electrical, physical and chemical parameters of the brain and the surrounding fluid are monitored. Additionally, the fluid can be modified, purified and recycled. When the patient has improved sufficiently such that the danger of brain swelling has subsided, usually in about 72 hours, the device is removed and the bone flaps are replaced.

In addition to treating brain injury from trauma, one skilled in the art will readily recognize that other brain injuries and/or diseases which require continual and/or repeated access to the brain can be treated with the cephalic expansion apparatus.

One skilled in the art will readily appreciate that the present invention is well adapted to carry out the objects and obtain the ends and advantages mentioned as well as those inherent therein. The methods, procedures, techniques, devices and apparatuses described herein are presently representative of the preferred embodiments and are intended to be exemplary and not intended as limitations on the scope. Changes therein and other uses which are encompassed within the spirit of the invention or defined by the scope of the appended claims will occur to those skilled in the art.

I claim:

1. An apparatus for the treatment of a swollen brain comprising:
    a flexible container for holding a volume of sterile fluid and an expanding brain of a craniotomized patient, the walls of said container forming an external, inferior surface for application to the scalp of the patient and an upper side having a flap formed therein for opening to expose the internal, inferior surface of said container when applied to the scalp;
    a plurality of access ports formed in the walls of said container for circulating the sterile fluid into and out of said container;
    means on the external, inferior surface of said container for water tight attachment of said container to the scalp of the patient;
    a circumferential expansion flap for increasing the volume of said container when filled with the sterile fluid;
    means on the flap formed in the upper side of said container for sealing said container to prevent the loss of the sterile fluid from said container; and
    a semicircular support rod for attachment to a stationary support for encircling a portion of the head of the patient and engaging the external, inferior surface of said container to support said container when filled with the sterile fluid.

2. The apparatus of claim 1 wherein said attachment means comprises a plurality of contact strips on the inferior surface of said container for forming a water tight seal with the scalp of the patient after the patient is craniotomized.

3. The apparatus of claim 1 further comprising a tube attached to one or more of said access ports for Introducing and draining the sterile fluid from said container.

4. The apparatus of claim 3 further comprising, means for regulating the temperature of the sterile fluid passing into and out of said container through the tube attached to said access ports.

5. A method of treating pathological swelling of the brain to prevent injury to the brain from increased intracranial pressure caused by swelling comprising the steps of:
   adhering the exterior, inferior surface of a container formed of an inferior surface and an upper side to the scalp of a patient to form a water-tight seal between the container and the scalp;
   opening a flap formed in the upper side of the container;
   performing a craniotomy through the open flap of the container by incising the internal, inferior surface of the container and the adherent scalp;
   sealing the container by closing the open flap to provide a closed container having a larger volume than the volume of the skull to allow the brain to expand into the container without an increase in the pressure on the brain; and
   filling the container with a sterile, pH adjusted fluid.

6. The method of claim 5 additionally comprising applying a plurality of contact strips to the scalp of the patient, each strip having a biological adhesive applied thereto, and adhering the container to the contact strips on the scalp of the patient.

7. The method of claim 5 further comprising circulating the sterile fluid into and out of the container.

8. The method of claim 7 further comprising the step of filtering the sterile fluid.

9. The method of claim 5 further including incising the internal, inferior surface of the container through the open flap to expose the cranium of the patient without affecting the seal between the container and the scalp.

10. The method of claim 5 wherein the container is adhered to the scalp of the patient by applying a biological adhesive to the scalp of the patient and then applying the exterior, inferior surface of the container to the portion of the scalp of the patient to which the biological adhesive has been applied.

11. The method of claim 6 wherein the craniotomy is performed by cutting through the contact strips, the contact strips and the incised edges of the scalp of the patient forming a water-tight seal.

12. A cephalic expansion apparatus for prevention of pressure-induced injury to the brain of a patient comprising:
   a container having a shape adapted to fit the head of a patient formed of walls having an inferior and an upper surface;
   a plurality of contact strips on the portion of the exterior inferior surface of said container which contacts the scalp of the patient when said container is applied to the head of the patient, said contact strips including a biological adhesive for forming a water-tight seal between the scalp and said container when in contact with the scalp of the patient;
   a first flap having sealing means formed in the wall of the upper surface of said container and movable between a first, open position for allowing access to the internal, inferior surface of said container for performance of a craniotomy on the patient by incising the internal, inferior surface of said container and the scalp through the contact strips and a second, sealed position for closing said container after performance of the craniotomy to form a closed, sterile environment in which the brain of the patient can expand without an increase in the pressure exerted on the brain; and
   a plurality of access ports for circulating a sterile fluid into and out of said container.

13. The apparatus of claim 12 additionally comprising an expansion flap formed in the walls of said container adjacent the portion of the inferior surface of said container which contacts the scalp of the patient for allowing the expansion of said container when the sterile fluid is circulated therethrough.

14. The apparatus of claim 12 wherein each of said access ports is adapted for receiving either a tube for circulation of the sterile fluid, a probe for monitoring the brain, means for monitoring the physical-chemical parameters in the fluid within the said container, or a ring for preventing inadvertent tube and probe movement and the cortical injury resulting therefrom.

15. The apparatus of claim 12 wherein the upper surface of said container is additionally comprised of a second flap having means located thereon for forming a water-tight seal with the first flap when the first flap is in said second position.

16. The apparatus of claim 15 wherein the first and second flaps formed in the upper surface of said container are provided with locking grooves for sealing said container closed.

17. The apparatus of claim 12 additionally comprising a semicircular support rod for encircling a portion of the head of the patient to support said container when filled with the sterile fluid and means for securing said support rod to a stationary support.

18. The apparatus of claim 17 wherein said support rod engages the inferior surface of said container adjacent the portion of the inferior surface which contacts the scalp of the patient.

* * * * *